United States Patent
Sampson et al.

(10) Patent No.: US 10,617,716 B2
(45) Date of Patent: Apr. 14, 2020

(54) HYPOCHLOROUS ACID FORMULATIONS AND METHODS FOR TREATING SKIN CONDITIONS

(71) Applicant: REALM THERAPEUTICS, INC., Malvern, PA (US)

(72) Inventors: Mark Sampson, Malvern, PA (US); Svetlana Panicheva, Malvern, PA (US); Cary Schockemoehl, Malvern, PA (US)

(73) Assignee: URGO US, INC., Fort Worth, TX (US)

( * ) Notice: Subject to any disclaimer, the term of this patent is extended or adjusted under 35 U.S.C. 154(b) by 0 days.

(21) Appl. No.: 15/535,555

(22) PCT Filed: Dec. 16, 2015

(86) PCT No.: PCT/US2015/066147
§ 371 (c)(1),
(2) Date: Jun. 13, 2017

(87) PCT Pub. No.: WO2016/100543
PCT Pub. Date: Jun. 23, 2016

(65) Prior Publication Data
US 2017/0360832 A1    Dec. 21, 2017

Related U.S. Application Data

(63) Continuation of application No. 14/670,641, filed on Mar. 27, 2015, now Pat. No. 9,999,635, which is a
(Continued)

(51) Int. Cl.
*A61K 33/20* (2006.01)
*A61K 45/06* (2006.01)
(Continued)

(52) U.S. Cl.
CPC .............. *A61K 33/20* (2013.01); *A61K 45/06* (2013.01); *A61K 9/0014* (2013.01); *A61K 9/06* (2013.01); *A61K 9/08* (2013.01); *A61K 2300/00* (2013.01)

(58) Field of Classification Search
CPC ...... A61K 33/20; A61K 45/06; A61K 9/0014; A61K 9/06; A61K 2300/00; A61K 9/08;
(Continued)

(56) References Cited

U.S. PATENT DOCUMENTS

| | | |
|---|---|---|
| 6,333,054 B1 | 12/2001 | Rogozinski |
| 8,871,278 B2 | 10/2014 | Panicheva et al. |

(Continued)

FOREIGN PATENT DOCUMENTS

| | | |
|---|---|---|
| CN | 101405012 A | 4/2009 |

OTHER PUBLICATIONS

Prurigo Nodularis Support, 2010, Prurigo Nodularis Support, https://www.tapatalk.com/groups/prurigonodularissupport/highly-suggest-this-bath-t1050.html, pp. 1-20. (Year: 2010).*

(Continued)

*Primary Examiner* — Trevor Love
(74) *Attorney, Agent, or Firm* — Morgan, Lewis & Bockius LLP

(57) ABSTRACT

The present invention in various aspects and embodiments provides methods and formulations for treating inflammatory conditions of the skin and/or conditions involving compromised skin barrier function. Such diseases include blistering diseases of the skin, hereditary defects in skin barrier function, hyperproliferative conditions involving the skin, conditions associated with aging or damaged skin, immunological disorders involving the skin, among others.

18 Claims, 1 Drawing Sheet

Related U.S. Application Data continuation of application No. 14/572,378, filed on Dec. 16, 2014, now Pat. No. 9,381,214.

(51) Int. Cl.

| | | |
|---|---|---|
| *A61K 9/00* | (2006.01) | |
| *A61K 9/06* | (2006.01) | |
| *A61K 9/08* | (2006.01) | |
| *A61P 35/00* | (2006.01) | |
| *A61P 35/04* | (2006.01) | |
| *A61P 29/00* | (2006.01) | |
| *A61P 37/00* | (2006.01) | |

(58) Field of Classification Search
CPC .......... A61P 35/00; A61P 35/04; A61P 29/00; A61P 37/00
See application file for complete search history.

(56) References Cited

U.S. PATENT DOCUMENTS

| | | | |
|---|---|---|---|
| 8,877,257 | B2 | 11/2014 | Goldan et al. |
| 9,381,214 | B2 | 7/2016 | Sampson et al. |
| 9,392,787 | B2 | 7/2016 | Panicheva et al. |
| 9,414,584 | B2 | 8/2016 | Panicheva et al. |
| 9,925,217 | B2 | 3/2018 | Sampson et al. |
| 9,999,635 | B2 | 6/2018 | Sampson et al. |
| 10,034,942 | B2 | 7/2018 | Panicheva et al. |
| 2006/0235350 | A1* | 10/2006 | Alimi .................. A61K 33/20 604/19 |
| 2009/0092685 | A1 | 4/2009 | Selkon |
| 2009/0258841 | A1 | 10/2009 | Murphy et al. |
| 2009/0305267 | A1 | 12/2009 | Krause et al. |
| 2012/0237616 | A1 | 9/2012 | Panicheva et al. |
| 2012/0251631 | A1 | 10/2012 | Alimi et al. |
| 2014/0134277 | A1 | 5/2014 | Panicheva et al. |
| 2015/0231173 | A1 | 8/2015 | Sampson et al. |
| 2018/0078578 | A1 | 3/2018 | Sampson et al. |
| 2018/0243335 | A1 | 8/2018 | Sampson et al. |

OTHER PUBLICATIONS

Lebwohl et al, Pathways to Managing Atopic Dermatitis: Consensus from the Experts, 2013, The Journal of Clinical and Aesthetic Dermatology, 6(7 Suppl): S2-S18. (Year: 2013).*

European Search Report and Written Opinion, European Application No. 15871006.1, dated Jun. 20, 2018, 8 pages.

Wang et al., "Hypochlorous Acid as a Potential Wound Care Agent Part I. Stabilized Hypochlorous Acid: A Component of the Inorganic Armamentarium of Innate Immunity", Journal of Burns and Wounds, vol. 6, 2007, pp. 65-79.

Erich Sandoval: "Onset Dermatologies Launches Aurstat(R) Kit", Feb. 2, 2812 (Feb. 2, 2812), XP855482725, Retrieved from the Internet: URL:http://www.marketwired.com/press-relea se/onset-dermatologics-launches-aurstat-kit-1625258.htm, [retrieved on 2018-86-08] abstract.

RI. Cumberland: "Onset Dermatologies Launches Patented Aurstat Anti-Itch Hydrogel 225mL", May 1, 2013 (2013-85-01), XP055482727, DOI: https://www.businesswire.com/news/home/201 38506805035/ en/Onset-Dermatologics-Launche s-Patented-Aurstat%C2%AE-Anti-Itch-Hydroge lRetrieved from the Internet:URL:http://api.elsevier.com/content/articl e/PII:0022282XI536320X?httpAccept=text/pl ain[retrieved on Jun. 8, 2018]The acd.

Pelgrift et al., Topical Hypochlorous Acid (HOCl) as a Potential Treatment of Pruritus, Curr Derm Rep (2013) 2:181-190.

Oaklander, Neuropathic Itch, Semin Cutan Med Surg. Jun. 2011; 30(2): 87-92.

Fukuyama et al., "Comparison of topical tofacitinib and 0.1% hypochlorous acid in a murine atopic dermatitis model", Fukuyama et al. BMC Pharmacology and Toxicology (2018) 19:37.

International Search and Written Opinion for International Application No. PCT2015/066147, dated Feb. 25, 2016, 13 pages.

* cited by examiner

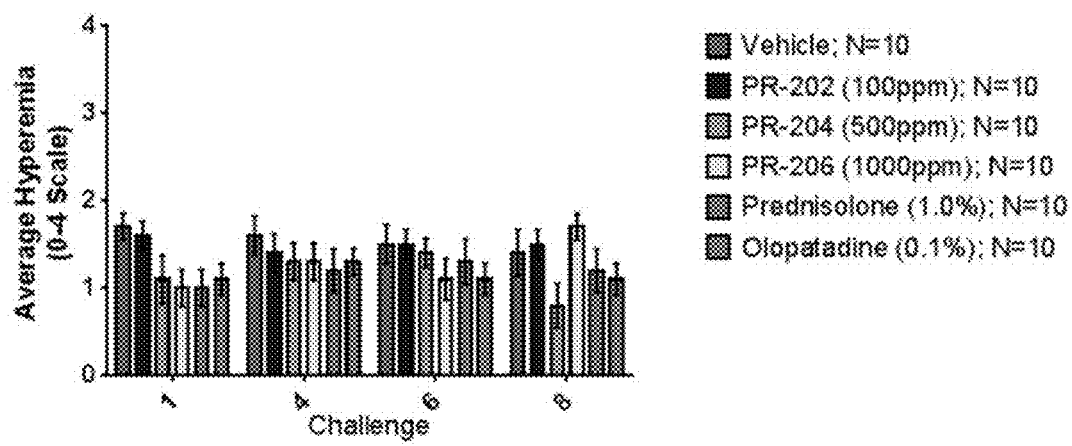
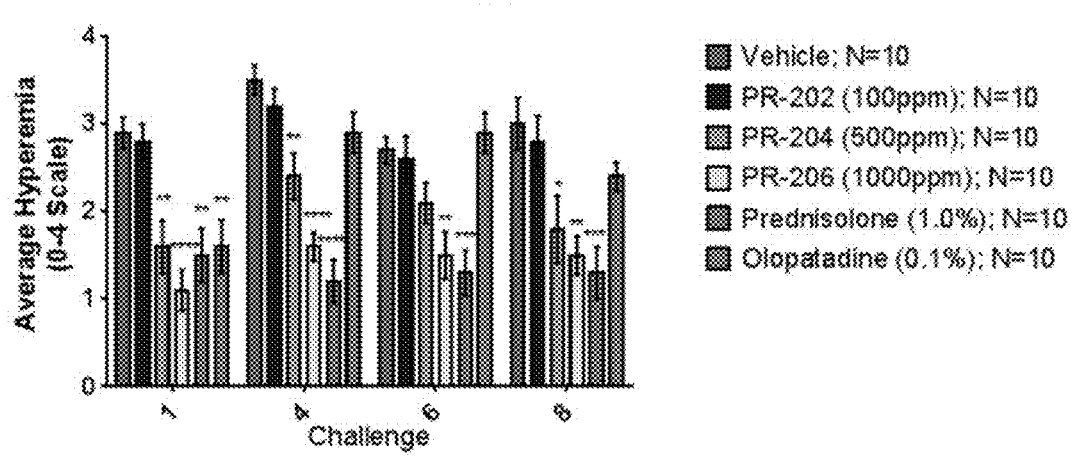

HYPOCHLOROUS ACID FORMULATIONS AND METHODS FOR TREATING SKIN CONDITIONS

RELATED APPLICATIONS

This application claims priority to U.S. application Ser. No. 14/572,378, filed Dec. 16, 2014, and to U.S. application Ser. No. 14/670,641, filed Mar. 27, 2015, each of which is hereby incorporated by reference in its entirety.

TECHNICAL FIELD

The present invention in various embodiments relates to formulations of hypochlorous acid (HOCl) and methods for the treatment of skin, for example, for the prevention, treatment, or maintenance of inflammatory or immune conditions, and/or for improvement in skin barrier function.

BACKGROUND

The skin acts as a barrier structure in vertebrates to protect from physical, chemical, and biological insult. For example, epidermal disruption exposes antigen presenting cells resident in the skin (e.g., Langerhans cells and dendritic cells) to environmental antigens, and further stimulates keratinocytes (as the first responders of the barrier insult) to release biological signals that lead to both activation and maturation of resident immune cells. The particular immune adjuvants released by keratinocytes can direct the character of the resulting immune response, including the induction of a Th2-type response, Th17-type response, or Th1-type response. See, for example, De Bennedetto, et al., *Skin Barrier Disruption—A Requirement for Allergen Sensitization, J. Invest. Dermatol.* 132(3):949-963 (2012).

Improving skin barrier function and modulating the underlying immunology is important in the prevention, treatment, and management of skin conditions, including: inflammatory conditions resulting from acute or chronic chemical, environmental, and/or biological insult; hereditary defects in skin barrier function; conditions associated with aging or damaged skin; proliferative disorders involving the skin; and immunological disorders of the skin or which manifest in symptoms that affect the skin, among other conditions.

The present invention meets these and other objectives.

SUMMARY OF THE INVENTION

The present invention in various aspects and embodiments provides methods of treating inflammatory conditions of the skin and/or conditions involving compromised skin barrier function. Such diseases include blistering diseases of the skin, hereditary defects in skin barrier function, proliferative conditions involving the skin, conditions associated with aging or damaged skin, immunological disorders involving the skin, among others. For example, the invention in various embodiments provides for methods of treating or managing conditions such as Bullous Pemphigoid, Epidermolysis Bullosa, Netherton Syndrome, Ichthyosis, Actinic Keratosis, pruritis, and skin cancers. In other embodiments, the conditions include those with an underlying immunological disorder or hypersensitivity, such as dermatitis (e.g., atopic dermatitis or contact dermatitis), psoriasis, dermatitis herpetiformis, and Systemic lupus erythematosus, among others. The invention in various embodiments comprises applying a hypochlorous acid formulation to the affected areas to thereby ameliorate disease symptoms and/or dampen or alter inflammatory responses (including systemic immune mediators). In some embodiments, the HOCl formulation inhibits or modulates immune responses, allowing skin to reach a more healthy immune state, including balancing of systemic immune mediators. As shown herein, hypochlorous acid can inhibit inflammatory processes according to a classic dose response.

In accordance with embodiments of the invention, the inflammatory condition may be present in a human or animal patient. In some embodiments, the patient is a pediatric or geriatric patient, or is immunocompromised. In some embodiments, the patient is refractory to corticosteroid treatment or treatment with other conventional agents, such as antihistamines, immunosuppressants and immunomodulators, retinoids, antibiotics (e.g., cyclosporine), among others.

In some embodiments, the patient is suffering from a blistering disease, such as but not limited to Bullous pemphigoid, Pemphigus, and Epidermolysis Bullosa, as well as blistering diseases that are the result of an autoimmune condition, such as dermatitis herpetiformis, or Systemic Lupus Erythematosus (SLE). These conditions involve impaired skin barrier function and persistent activation of inflammatory and immune processes that further exacerbate the condition.

In some embodiments, the condition is a hereditary defect in skin barrier function, such as Netherton Syndrome, Ichthyosis, and palmoplantar hyperkeratinosis. These conditions can result in persistent activation of inflammatory and immune processes in the skin resulting in considerable suffering and morbidity.

In some embodiments, the condition is a proliferative condition involving the skin, such as squamous cell carcinoma, basal cell carcinoma, or cutaneous T-cell Lymphoma. Tumor development in the skin is accompanied by an immune response that leads to tumor infiltration by inflammatory cells, and consequently, local and systemic production of cytokines, chemokines and other mediators. These inflammatory mediators are associated with cancer development.

In some embodiments, the condition is a result of, or is associated with, aging or damaged skin, such as Actinic keratosis, or UV damage, or other physical damage to the skin barrier that results in a hypersensitivity reaction.

In some embodiments, the condition is immunological in nature, such as atopic dermatitis or contact dermatitis, psoriasis, dermatitis herpetiformis, sarcoidosis, SLE, Sjogren's Syndrome, or allergic reaction. In these embodiments, the hypochlorous acid formulation helps to heal and prevent lesions, while dampening or altering the underlying skin and/or systemic immunology.

In various embodiments, the hypochlorous acid is applied as an alternative or adjunct therapy to conventional treatments with corticosteroids, vitamin D ointment (or vitamin D analogue), retinoid, analgesic, immunosuppressant, phototherapy, antihistamine, and anti-infective agent (e.g., antibiotic or antifungal), for example.

In other aspects, the invention provides hypochlorous acid formulations for treating inflammatory disorders involving skin. The hypochlorous acid formulation has available free chlorine (AFC) in the range of from about 100 ppm to about 3000 ppm. In some embodiments, the formulation has an AFC in the range of about 500 to about 2000 ppm, or in the range of about 500 to about 1500 ppm, or in the range of about 500 ppm to about 1000 ppm. The formulation may have a pH of from about 4.0 to about 7.5, but in certain embodiments has a pH of from about 4.4 to about 7.0, or a pH of about 5 to about 7, or a pH of from about 5.4 to about 6.4, or a pH of from about 5.0 to about 6.4. The pH ensures that hypochlorous acid is the predominant oxidant species, and that the formulation will help maintain a "skin-friendly" pH that is conducive to healing processes and/or healthy skin microbiome.

The formulation further comprises components to render the formulation shelf-stable and to provide the desired physical characteristics for topical treatment of skin. For example, a hypochlorous acid solution can be used as a dispersing media with a silicate carrier to prepare an HOCl hydrogel. For example, the formulation may be a hydrogel having a conductivity of from about 0.5 mS/cm to about 12 mS/cm, such as from about 1 mS/cm to about 10 mS/cm in some embodiments. The HOCl hydrogel may be prepared from silicate-based carriers, such as about 0.5% to about 5% of a fluorosilicate-based carrier, and may employ additional agents for targeting and maintaining the pH, such as phosphoric acid and sodium bicarbonate.

In some embodiments, the formulation is a hydrogel employing a fluorosilicate-based carrier, comprises sodium bicarbonate (e.g., from 500 to 2000 mg/L) to stabilize the HOCl, and comprises phosphoric acid to target an acidic pH (e.g., from 5 to 6.5). The formulation may have a viscosity of from about 500 to about 150,000 cP, such as from about 1000 to about 80,000 cP, or from about 1000 to about 40,000 cP. The formulation in some embodiments has a conductivity of less than 10 mS/cm, such as from about 0.5 to about 5 mS/cm, or from about 0.5 to about 3 mS/cm, or about 1 or about 2 mS/cm in some embodiments.

Other aspects and embodiments of the invention will be apparent to the skilled artisan based on the following detailed description.

DESCRIPTION OF THE FIGURES

FIG. 1 shows the ability of HOCl formulations to reduce hyperemia in an animal model according to a classic dose response. Treatment with steroid (prednisolone) and antihistamine (olopatadine) are shown as comparators. (A) 1 hour post-dose hyperemia; (B) 18 minutes post-CAC (conjunctival allergen challenge) hyperemia.

DETAILED DESCRIPTION

The present invention in various aspects and embodiments provides methods of treating inflammatory conditions of the skin and/or conditions involving compromised skin barrier function. Such diseases include blistering diseases of the skin, hereditary defects in skin barrier function, hyperproliferative conditions involving the skin, conditions associated with aging or damaged skin, immunological disorders involving the skin, among others. For example, as described more fully below, the invention in various embodiments provides for methods of treating or managing conditions such as Bullous Pemphigoid, Epidermolysis Bullosa, Netherton Syndrome, Ichthyosis, Actinic Keratosis, pruritis, and skin cancers. In other embodiments, the conditions include those with an underlying immunological disorder or hypersensitivity, such as dermatitis (e.g., atopic dermatitis or contact dermatitis), psoriasis, dermatitis herpetiformis, and Systemic lupus erythematosus, among others.

The invention in various embodiments comprises applying a hypochlorous acid formulation, as described more fully herein, to the affected areas to thereby ameliorate disease symptoms and/or dampen or alter inflammatory responses. Cells directing the immune response include keratinocytes at the site of skin barrier insult, which secrete cytokines and other soluble factors that may include, for example, one or more of TNF, IFNγ, IL-1β, IL-2, IL-4, IL-6, IL-8, IL-10, IL-18, among others. Cytokine release patterns vary, both between cytokines as well as cell types. For example, many immune mediators are secreted through classical secretory pathways including regulated or constitutive exocytosis or by degranulation. In classical secretory pathways, cytokines are translated with signal peptides in the endoplasmic reticulum (ER), trafficked in vesicles to the golgi complex, and subsequently to the cell surface for release. In the case of degranulation, cytokines and/or other cargo are stored in granules for later release. On the other hand, certain cytokines, such as IL-1β and IL-18, which are activated by the inflammasome and play a basic role in the initiation of inflammatory responses, are secreted via non-classical secretory pathways. Specifically, these molecules are synthesized as inactive precursors, and once activated by caspase-1 cleavage, are potentially secreted either by membrane transporters, in exosomes or microvesicles, or perhaps even by cell lysis. See, for example, Lacy and Stow, *Cytokine release from innate immune cells: association with diverse membrane trafficking pathways, Blood* 118(1) (July, 2011).

While the role of endogenous reactive oxygen species (ROS) in the inflammatory process has been somewhat clouded by conflicting data, ROS are generally considered as activators of the inflammasome. See, Harijith A, et al., *Reactive oxygen species at the crossroads of inflammasome and inflammation, Front. Physiol.* 5:352 (2014). For example, endogenously generated hypochlorous acid is generally regarded as a pro-inflammatory molecule. See, Schieven G L et al., *Hypochlorous acid activates tyrosine phosphorylation signal pathways leading to calcium signaling and TNFalpha production, Antioxid. Redox Signal* 4(3): 501-7 (2002); Pullar J L, et al., *Living with a killer: the effects of hypochlorous acid on mammalian cells, IUBMB Life,* 50(4-5):259-66 (2000). HOCl generation in vivo has been postulated to mediate inflammation in chronic inflammatory disease. Halliwell et al., *Oxidants, inflammation, and anti-inflammatory drugs, FASEB* 2:2867-2873 (1988). In contrast, the present disclosure shows that HOCl can inhibit inflammatory processes according to a classic dose response. Further, HOCl can reduce or alter the underlying immune response, including reducing or altering the systemic immune response.

In accordance with the invention, hypochlorous acid (a strong oxidant) is formulated for application to the skin for treatment of acute and chronic inflammatory conditions and diseases. While topical and systemic steroids are the most commonly prescribed medications for the treatment of inflammatory skin diseases, there is increasing awareness to the side effects and damage that can result from long term steroid use, which include increased appetite, weight gain, sudden mood swings, muscle weakness, blurred vision, increased growth of body hair, easy bruising, lower resistance to infection, swollen, puffy face, acne, osteoporosis, worsening of diabetes, high blood pressure, stomach irritation, nervousness, restlessness, difficulty sleeping, cataracts or glaucoma and water retention or swelling, among others. Topical retinoid, topical vitamin D (and analogues thereof), antihistamine, and immunosuppressants are used for some dermatological conditions, but these agents can be associated with substantial toxicity. Further, some patients and conditions are refractory to available treatments. Thus, more effective and/or safe alternatives are desirable. The hypochlorous acid formulation described herein may be used as an alternative or adjunct therapy to these agents.

The hypochlorous acid formulation in various embodiments of the present invention comprises an amount of hypochlorous acid that is effective to reduce or inhibit inflammatory and/or immune processes. In some embodiments, the formulation has available free chlorine (AFC) in the range of from about 100 ppm to about 3000 ppm. For example, the AFC of the formulation may be at least about 150 ppm, at least about 200 ppm, at least about 250 ppm, at least about 300 ppm, at least about 400 ppm, at least about 500 ppm, at least about 700 ppm, at least about 800 ppm, at least about 900 ppm, or at least about 1000 ppm, or at least about 1200 ppm, or at least about 1500 ppm. In some embodiments, the formulation has an AFC in the range of about 500 to about 2000 ppm, or in the range of about 500 to 1200 ppm, or in the range of about 500 to about 1500 ppm, or in the range of about 500 ppm to about 1000 ppm. In other embodiments, the formulation may have AFC of from about 100 to 1000 ppm, or about 100 to 500 ppm. In some embodiments described herein, the HOCl formulation has AFC in the range of 400 to 1000 ppm.

The formulation may comprise a mixture of oxidizing species such as predominantly hypochlorous acid and sodium hypochlorite. Hypochlorous acid and hypochlorite are in equilibrium and the position of the equilibrium is determined predominately by the pH (that is, pH effects the concentration of each component). A formulation with a pH of 5.1 to 6.0 has a purity of about ≥95% hypochlorous acid. Thus, the formulation may have a pH of from about 4.0 to about 7.5, but in certain embodiments has a pH of from about 4.4 to about 7.0, or a pH of about 5 to about 7, or a pH of from about 5.4 to about 6.4, or a pH of from about 5.0 to about 6.4. At a pH of about 5.4 the formulation will contain mostly (close to 100%) hypochlorous acid with respect to hypochlorite.

In certain embodiments, the formulation contains at least 80% hypochlorous acid relative to the total concentration of hypochlorous acid, hypohalite, and molecular chlorine ($Cl_2$) (as 100%). The hypochlorous acid may have, however, at least 90%, at least 95%, or at least 98% hypochlorous acid relative to the total concentration of hypochlorous acid, hypohalite, and molecular chlorine ($Cl_2$) (as 100%). Such embodiments may allow for higher levels of active chlorine to be administered, while avoiding any irritation as a result of the formulation. Hypochlorite has been known for quite some time to have toxic properties on mammalian cells due to high pH in addition to required concentration of available chlorine, and thus may not be desirable for long term use or may not have a sufficient therapeutic window for many anti-inflammatory applications. Thus, in some embodiments, the level of hypochlorite in the composition is limited (e.g., about 10% or less, about 5% or less, or about 3% or less relative to the total concentration of hypochlorous acid, hypochlorite, and $Cl_2$ (as 100%)). While the formulation may comprise, or consist essentially of hypochlorous acid as the active agent, in some embodiments, the formulation contains minor amounts of other oxidizing or radical producing species such as a hypochlorite, hydroxide, $H_2O_2$ and $O_3$, among others.

In accordance with the invention, the hypochlorous acid formulation can be administered to a patient for treating a variety of inflammatory conditions. As used herein, the term "treating" refers to providing therapy to a patient to prevent (by means of prophylactic treatment), reduce, inhibit, ameliorate, or manage symptoms (e.g., inflammatory symptoms) of a disease, or to slow or stop progression of the disease, as well as in some embodiments, to prevent onset or re-occurrence of a condition or symptom. For example, in various embodiments the invention provides methods of treating skin to inhibit, reduce, prevent, or alter inflammatory processes including acute, chronic, and delayed reactions, thereby allowing regeneration and/or healing of tissues, and/or preventing tissue damage or loss of tissue integrity.

In some embodiments, the invention provides methods for treating chronic inflammation. Chronic inflammation can last for weeks to months, and possibly years, in which tissue destruction and biological processes that are intended to repair injury are simultaneously ongoing. Chronic inflammation can involve lymphocytes, macrophages, and keratinocytes, and may also include a proliferation of blood vessels, fibrosis and/or necrosis. Chronic inflammation can result from a number of factors including persistent infections, prolonged exposure to toxic agents, genetic malady, and autoimmune reactions. Chronic inflammation is often maintained by the production of cytokines at the site of the persistent insult.

In some embodiments, the patient is suffering from a blistering disease, such as but not limited to Bullous pemphigoid, Pemphigus, and Epidermolysis Bullosa, as well as blistering diseases that are the result of an autoimmune condition, such as dermatitis herpetiformis, or Systemic Lupus Erythematosus (SLE). These conditions involve impaired skin barrier function and persistent activation of inflammatory and immune processes that further exacerbate the condition.

Bullous pemphigoid is an acute or chronic autoimmune skin disease, involving the formation of blisters (or bullae), at the space between the epidermis and dermis. It is classified as a type II hypersensitivity reaction. The earliest lesions may appear urticarial, but tense bullae eventually erupt. The bullae are formed by an immune reaction, initiated by the formation of IgG autoantibodies targeting Dystonin (Bullous Pemphigoid Antigen) and/or type XVII collagen (Bullous Pemphigoid Antigen 2), which is a component of hemidesmosomes. Following antibody targeting, a cascade of immunomodulators results in a surge of immune cells, including neutrophils, lymphocytes and eosinophils coming to the affected area, ultimately resulting in a separation along the dermoepidermal junction and eventually stretch bullae. Conventional treatments for Bullous pemphigoid include topical or systemic steroids, or immunosuppressants for more difficult cases.

Epidermolysis bullosa (EB) refers to a group of inherited connective tissue diseases that cause blisters in the skin and mucosal membranes. EB is a result of a defect in anchoring between the epidermis and dermis, resulting in friction and skin fragility. Epidermolysis bullosa simplex is a form of EB that manifests blisters at the site of rubbing, typically affecting the hands and feet. Junctional epidermolysis bullosa is an inherited disease affecting laminin and collagen, and is characterized by blister formation within the lamina lucida of the basement membrane zone. It also presents with blisters at the site of friction, especially on the hands and feet. Dystrophic epidermolysis bullosa is an inherited variant affecting the skin and other organs, and is caused by mutations within the human COL7A1 gene encoding type VII collagen. As a complication of the chronic skin damage and underlying immune abnormalities, people suffering from EB have an increased risk of malignancies of the skin and persistent infection. Treatment often involves glucocorticoids and topical antibiotics, with the goal of aiding healing of wounds and lesions. The healing process in these patients may be genetically impaired.

Dermatitis herpetiformis (DH) is a chronic blistering skin condition characterized by blisters filled with a watery fluid. DH is a specific manifestation of celiac disease. Dermatitis herpetiformis is characterized by intensely itchy, chronic papulovesicular eruptions, usually distributed symmetrically on extensor surfaces, such as buttocks, back of neck, scalp, elbows, knees, back, hairline, groin, or face. The condition is extremely itchy. Although the first signs and symptoms of dermatitis herpetiformis are intense itching and burning, the first visible signs are the small papules or vesicles. Dermatitis herpetiformis symptoms are chronic, and they tend to come and go. Symptoms may be accompanied by symptoms of celiac disease, commonly including abdominal pain, bloating or loose stool, and fatigue. In terms of pathology, the first signs of the condition may be observed within the dermis. The main autoantigen of dermatitis herpetiformis is epidermal transglutaminase (eTG), a cytosolic enzyme involved in cell envelope formation during keratinocyte differentiation. While immunosuppressive therapies are sometimes administered to help control the condition (and are not terribly effective), DH is ultimately controlled by strict adherence to a gluten-free diet (GFD). Strict adherence to a GFD is difficult, and some patients remain refractory to GFD with underlying immune activation.

Systemic lupus erythematosus (SLE or lupus) is a systemic autoimmune disease. SLE most often harms the heart, joints, skin, lungs, blood vessels, liver, kidneys, and nervous system. The course of the disease is unpredictable, with periods of illness (flare-ups) alternating with remissions. Dermatological symptoms are observed in as many as 70% of people with lupus. The three main categories of lesions are chronic cutaneous (discoid) lupus, subacute cutaneous lupus, and acute cutaneous lupus. People with discoid lupus may exhibit thick, red scaly patches on the skin. Similarly, subacute cutaneous lupus manifests as red, scaly patches of skin but with distinct edges. Acute cutaneous lupus manifests as a rash. Some have the classic malar rash (or butterfly rash) associated with the disease. Treatment or management of dermatological lupus symptoms can include corticosteroid creams for skin rashes.

In some embodiments, the condition is a hereditary defect in skin barrier function, including (in addition to those described above), Netherton Syndrome, Ichthyosis, and palmoplantar hyperkeratinosis. These conditions can result in persistent activation of inflammatory and immune processes in the skin resulting in considerable suffering and morbidity.

Netherton Syndrome is a severe, autosomal recessive form of ichthyosis associated with mutations in the SPINK5 gene. Netherton syndrome is characterized by chronic skin inflammation, universal pruritus (itch), severe dehydration, and stunted growth. Patients with this disorder tend to have a hair shaft defect (trichorrhexis invaginata), also known as "bamboo hair". The disrupted skin barrier function in affected individuals also presents a high susceptibility to infection and allergy, leading to the development of scaly, reddish skin similar to atopic dermatitis. In severe cases, these atopic manifestations persist throughout the individual's life, post-natal mortality rates are high. In less severe cases, this develops into the milder ichthyosis linearis circumflexa. Patients are more prone than healthy people to infections of all types, especially recurrent skin infections with *staphylococcus*. Current treatments include moisturizing products to minimize scaling/cracking, and anti-infective treatments to manage the persistent infections. Steroid and retinoid products are generally ineffective against Netherton Syndrome, and may even exacerbate the condition.

Ichthyosis is a family of mostly genetic skin disorders. All types of ichthyosis have dry, thickened, scaly or flaky skin. In many types there is cracked skin, which is said to resemble the scales on a fish. The severity of symptoms can vary enormously, from the mildest, most common, type such as ichthyosis vulgaris (which may be mistaken for normal dry skin) up to life-threatening conditions such as harlequin type ichthyosis. Ichthyosis vulgaris accounts for more than 95% of cases. Types of ichthyoses are classified by their appearance and their genetic cause. Ichthyosis caused by the same gene can vary considerably in severity and symptoms, and different genes can produce ichthyoses with similar symptoms. Treatments for ichthyosis often take the form of topical application of creams and emollient oils, in an attempt to hydrate the skin. Retinoids are also used in some cases.

Palmoplantar keratodermas (e.g., Palmoplantar hyperkeratosis) are a heterogeneous group of disorders characterized by abnormal thickening of the palms and soles. Clinically, three distinct patterns of palmoplantar keratoderma are diffuse, focal, and punctate. Diffuse palmoplantar keratoderma is characterized by an even, thick, symmetric hyperkeratosis over the whole of the palm and sole, usually evident at birth or in the first few months of life. Focal palmoplantar keratoderma, a type of palmoplantar keratoderma in which large, compact masses of keratin develop at sites of recurrent friction, principally on the feet, although also on the palms and other sites, a pattern of calluses that may be discoid or linear. Punctate palmoplantar keratoderma is a form of palmoplantar keratoderma in which many tiny keratoses involve the palmoplantar surface, skin lesions which may involve the whole of the palmoplantar surface, or may be more restricted in their distribution. Treatments often include emollients, topical retinoids, keratolytics, and topical vitamin D ointment (e.g., calcipotriol).

In some embodiments, the condition is a hyperproliferative condition involving the skin, such as squamous cell carcinoma, basal cell carcinoma, or cutaneous T-cell Lymphoma. Tumor development in the skin is accompanied by an immune response that leads to tumor infiltration by inflammatory cells, and consequently, local and systemic production of cytokines, chemokines and other mediators. These inflammatory mediators are associated with cancer development.

Squamous-cell carcinoma (SCC) is a cancer of the squamous cell, which is a main part of the epidermis of the skin. SCC is one of the major forms of skin cancer. However, squamous cells also occur in the lining of the digestive tract, lungs, and other areas of the body, and SCC occurs as a form of cancer in diverse tissues, including the lips, mouth, esophagus, urinary bladder, prostate, lung, vagina, and cervix, among others. The SCCs of different body sites can show tremendous differences in their presenting symptoms, natural history, prognosis, and response to treatment. SCC is a histologically distinct form of cancer. It arises from the uncontrolled multiplication of cells of epithelium, or cells showing particular cytological or tissue architectural characteristics of squamous-cell differentiation, such as the presence of keratin, tonofilament bundles, or desmosomes, structures involved in cell-to-cell adhesion. SCC of the skin begins as a small nodule and as it enlarges the center becomes necrotic and sloughs and the nodule turns into an ulcer. The lesion caused by SCC is often asymptomatic. The clinical appearance is highly variable. The tumor can lie below the level of the surrounding skin, and eventually ulcerates and invades the underlying tissue. The tumor commonly presents on sun-exposed areas. On the lip, the tumor forms a small ulcer, which fails to heal and bleeds intermittently. Unlike basal-cell carcinoma (BCC), SCC has a substantial risk of metastasis. Risk of metastasis is higher in SCC arising in scars, on the lower lips or mucosa, and occurring in immunosuppressed patients. SCC is generally treated by surgical excision, Mohs surgery or electrodessication and curettage. Non-surgical options for the treatment of cutaneous SCC include topical chemotherapy, topical immune response modifiers, photodynamic therapy (PDT), radiotherapy, and systemic chemotherapy. The use of topical therapy, such as Imiquimod cream and PDT is generally limited to premalignant and in situ lesions. Radiation therapy is a primary treatment option for patients in whom surgery is not feasible and is an adjuvant therapy for those with metastatic or high-risk cutaneous SCC. Systemic chemotherapy is used exclusively for patients with metastatic disease.

Basal-cell carcinoma (BCC) is another form of skin cancer. It rarely metastasizes or kills. However, BCC can cause significant destruction and disfigurement by invading surrounding tissues. Treatments include surgery, radiation, photodynamic therapy (PDT), as well as topical chemotherapy.

Cutaneous-T-Cell Lymphoma (CTLC) is a non-Hodgkin's lymphoma that may present with an intractable itch, and red and scaly skin. The stabilized hypochlorous acid formulation can provide a relief from the discomfort of skin irritation associated with CTCL.

In some embodiments, the condition is a result of, or is associated with, aging or damaged skin, such as Actinic keratosis, or UV damage, or other physical damage to the skin barrier that results in hypersensitivity reactions.

Actinic keratosis (AK) is a pre-cancerous patch of thick, scaly, or crusty skin. These growths are more common in fair-skinned people and those who are frequently in the sun. They usually form when skin gets damaged by ultraviolet (UV) radiation from the sun or indoor tanning beds. AKs are considered potentially pre-cancerous; left untreated, they may turn into a type of cancer (e.g., squamous cell carcinoma). Development of these growths occurs when skin is constantly exposed to the sun over time. They usually appear as thick, scaly, or crusty areas that often feel dry or rough. They may be dark, light, tan, pink, red, a combination of all these, or have the same color as the surrounding skin. An actinic keratosis lesion commonly ranges between 2 and 6 millimeters in size but can grow to be a few centimeters in diameter. They often appear on sun-exposed areas of the skin. Because they are related to sun-damage on the skin, most people who have an AK have more than one. Conventional treatments include 5-fluorouracil cream. In accordance with some embodiments, the HOCl formulation is effective against AK as a topical anti-inflammatory agent.

UV damage, e.g., resulting from too much sun exposure, can range from dry skin (as skin loses lose moisture and essential oils) and sunburn. Mild sunburn causes only painful reddening of the skin, but more severe cases can produce tiny fluid-filled bumps or larger blisters. Long term sun exposure can result in actinic keratosis. Treatments for UV damaged skin, when conventional moisturizers are insufficient, can include anti-inflammatory medications, such as ibuprofen or aspirin.

In some embodiments, the condition is immunological in nature, such as atopic dermatitis or contact dermatitis, psoriasis, dermatitis herpetiformis, sarcoidosis, SLE, Sjogren's Syndrome, or allergic reaction. In these embodiments, the hypochlorous acid formulation helps to heal and prevent lesions, while dampening and/or altering the underlying skin immunology.

Atopic dermatitis (AD), also known as atopic eczema, results in itchy, red, swollen, and cracked skin. Clear fluid may come from the affected areas, which often thicken over time. It typically starts in childhood with changing severity over the years. In children under one year of age much of the body may be affected. As they get older the back of the knees and front of the elbows are the most common area for the rash. In adults the hands and feet are most affected. Scratching worsens symptoms and affected people have an increased risk of skin infections. Many people with atopic dermatitis develop hay fever or asthma. The cause is unknown but believed to involve genetics, immune system dysfunction, environmental exposures, and difficulties with the permeability of the skin. The diagnosis is typically based on the signs and symptoms. Conventional treatment involves avoiding things that make it worse, daily bathing with application of a moisturizing cream afterwards, applying steroid creams when flares occur, and medications to help with itchiness. Phototherapy may be useful in some people. Oral steroid may occasionally be used if other measures are not effective. Antibiotics (either by mouth or topically) may be administered if a bacterial infection develops.

Psoriasis is a long-lasting autoimmune disease characterized by patches of abnormal skin. These skin patches are typically red, itchy, and scaly. They may vary in severity from small and localized to complete body coverage. Injury to the skin can trigger psoriatic skin changes at that spot. There are five main types of psoriasis: plaque, guttate, inverse, pustular, and erythrodermic. Plaque psoriasis, also known as psoriasis vulgaris, makes up about 90% of cases. Topical agents are typically used for mild disease, phototherapy for moderate disease, and systemic agents for severe disease. Benefit has been observed with potent corticosteroids. Vitamin D analogues are effective in some cases, which can be combined with corticosteroid therapy. Moisturizers and emollients are used to help clear psoriatic plaques, sometimes in combination with phototherapy.

The majority of psoriasis patients experience a recurrence of psoriasis after systemic treatment is discontinued. Non-biologic systemic treatments frequently used for psoriasis include methotrexate, cyclosporine, hydroxycarbamide, fumarates such as dimethyl fumarate, and retinoids. Methotrexate and cyclosporine are drugs that suppress the immune system; retinoids are synthetic forms of vitamin A. These agents are also regarded as first-line treatments for psoriatic erythroderma. Several monoclonal antibodies targeting TNF-α have been developed for treatment of psoriasis (e.g., infliximab, adalimumab, golimumab, and certolizumab pegol) and one recombinant TNF-α decoy receptor, etanercept. Additional monoclonal antibodies have been developed against pro-inflammatory cytokines interleukin-12, interleukin-23 and interleukin-17, which inhibit the inflammatory pathway at a different point than the anti-TNF-α agents. Two drugs have been developed that target T cells (efalizumab and alefacept). Individuals with psoriasis may develop neutralizing antibodies against these biologic agents. Further, treatment with these agents is expensive.

In some embodiments, the patient has pruritus, which in some embodiments is associated with an underlying skin or immunological condition, including those mentioned above. The hypochlorous acid formulation can be administered to combat itch, including where there is no discernible (e.g., objective) inflammatory reaction or irritant. For example, such condition may result from sensitive skin in combination with physical factors (such as ultraviolet radiation, heat, cold, wind), general chemical stress (e.g., cosmetics, soap, water, pollution), physiological stress or disorder, substance abuse, hormonal conditions (e.g., menstrual cycle), or other systemic malady. Even in the absence of an objective perception of skin inflammation, the hypochlorous acid is useful for reducing the subjective stinging, burning, warmth and tightness associated with itch (e.g., pruritus). For example, in some embodiments, the subject has or is determined to have a psychogenic itch, which can be associated with for example substance abuse or withdrawal, psychosis, mania, depression, stress, anxiety, or obsessive compulsive disorder. In other embodiments, the itch is a neurogenic itch that is, for example, secondary to disease occurring in places other than the skin such as hematologic disorder (polycythemia vera), lymphoproliferative diseases (e.g., leukemia, Hodgkin Lymphoma, Sezary syndrome), cholestasis, hepatic disease, endocrine disease, or chronic kidney disease. In some embodiments, the patient has prurigo nodularis, which is a skin disease characterized by pruritic (itchy) nodules. Patients often present with multiple excoriated lesions caused by scratching. In other embodiments, the hypochlorous acid formulation is administered to combat the itch associated with ichthyosis.

The hypochlorous acid formulation is useful for treating inflammation that results from, for example, one or a combination of contact with noxious substances, genetic malady affecting the skin, injury (e.g., impaired or damaged skin, including that resulting from persistent scratching), infection, autoimmune reaction, systemic autoimmune reaction manifesting in itching and/or hives, immune deficiency, hypersensitivity (of Type I, II, III, or IV), allergic reaction, including allergic reactions associated with cellular histamine and pro-inflammatory cytokines. Additional conditions, in which the hypochlorous acid formulation can be beneficial, include sarcoidosis involving the skin, pemphigus (e.g., vulgaris or folioceus), erythema multiforme, urticaria (including chronic urticaria), Selective Immunoglobulin M Deficiency, Hidrontic Ectodermal Dysplasia (HED), Sjogrren's Syndrome, contact dermatitis, rosacea (including of treatment of inflammatory lesions associated with rosacea), acne (including inflammatory acne), and skin allergy. In some embodiments, the hypochlorous acid formulation relieves itch and discomfort from the disorder, and may provide general relief from symptoms and reduce the severity of disease. In some embodiments, the hypochlorous acid is administered to a human or animal for skin pathogen disinfection, including bacteria, mycoplasmas, virus, or fungi, including skin fungi such as athlete's foot. In some embodiments, the hypochlorous acid formulation treats or prevents over-colonization of commensal microbes such as *Staphylococcus*, to obtain and/or maintain a healthy skin microbiome. These embodiments can be important for maintenance or treatment of some conditions such as atopic dermatitis or psoriasis, among others where the skin microbiome is characterized by overgrowth of commensal organisms.

In various embodiments, the hypochlorous acid is applied as an alternative or adjunct therapy to conventional treatments with corticosteroids, vitamin D ointment (or vitamin D analogue), retinoid, analgesics, immunosuppressant, phototherapy, antihistamine, anti-infectives (e.g., antibiotic or antifungal), or biologic in the case of psoriasis, for example. Without limitation, various conventional treatments for indications are disclosed herein. In some embodiments, the HOCl formulation is used in place of a corticosteroid.

The inflammatory condition may be present in a human or animal patient of any age (including pediatric and geriatric patients) and/or in an immunocompromised patient. Exemplary animal patients include mammals such as dogs, cats, horses, lamb, cattle, goats, pigs, and guinea pigs. In various embodiments, the patient is a human patient. The present invention further contemplates preventive care (including prophylactic use) for such inflammatory conditions or prevention of such conditions where the patient is genetically or environmentally pre-disposed to such conditions, as well as conditions that don't completely resolve with antimicrobial or steroidal treatment, or treatment with retinoid, vitamin D ointment, immunosuppressant, or biologic anti-inflammatory agent. Pediatric patients include infants, children, and adolescents, and the age limit usually ranges from birth up to 18 years of age (age 21 in the United States). In some embodiments, the patient is under 12 years of age, or is an infant. Geriatric patients in accordance with this disclosure include individuals over the age of 60. Immunocompromised patients include those having an immune response attenuated by administration of immunosuppressive drugs, chemotherapy, by irradiation, by malnutrition, genetic malady, or by certain disease processes such as acquired immunodeficiency syndrome (AIDS).

In some embodiments, the affected areas of the skin may be characterized by an alkaline pH as compared to normal healthy skin. In such embodiments, the weak—acidic pH of the hypochlorous acid helps bring the skin to a pH that is more conducive to healing and healthy regeneration. In some embodiments, a more alkaline skin is associated with over-colonization of certain microbes (e.g., *Staphylococcus* sp.), whereas a slightly acidic pH is more conducive to a healthy skin microbiome. Further, in some embodiments, application to intact but inflamed skin promotes healthy skin regeneration and barrier integrity, by inhibiting or reducing the tissue-damaging inflammatory response, thereby allowing the cells (e.g., dermal fibroblasts and/or keratinocytes) to proliferate in a manner consistent with the healing process. Further still, HOCl is not cytotoxic to these cells at the levels applied. The healing environment is further aided by reducing the microbial burden of the inflamed tissue, where otherwise infection might spawn due to loss of barrier integrity. Thus, in various embodiments, the hypochlorous acid formulation results in one or more of a reduction of microbial burden, a reduction of inflammation, altered or balanced skin and/or systemic immunity, reduced pruritis, enhanced skin cell regeneration, and normalized skin pH.

The hypochlorous acid formulation may be applied to affected areas as needed to combat and/or control disease symptoms (including itch), or may be applied using a more precise regimen, such as about daily, or from 1 to about 10 times daily, or from 1 to about 5 times daily, or from 1 to about 3 times daily (e.g., about twice daily).

In some embodiments, the hypochlorous acid formulation is applied periodically to control symptoms or flare-ups, such as a regimen of the formulation that lasts for 1 to about 12 weeks, or for 1 to about 10 weeks, or for 1 to about 8 weeks, or for 1 to about 6 weeks, or for 1 to about 4 weeks. In some embodiments, the regimen lasts for about 1 or 2 weeks. In some embodiments, the hypochlorous acid formulation is used between flare-ups to prevent or reduce the severity and/or frequency of symptom flare-ups (e.g., formation of blisters, bumps, lesions, or itch). In these or other embodiments, the hypochlorous acid formulation is used between (but not simultaneously with) conventional treatments such as corticosteroid, immunosuppressant, topical vitamin D, retinoid, and/or antibiotic. In some embodiments, the HOCl formulation is used alongside topical or oral corticosteroid, and in some embodiments, allows for lower dose or frequency of steroid use. In some embodiments, the HOCl is used in place of a corticosteroid, thereby allowing for prolonged use without side effects associated with corticosteroid use.

In some embodiments, the hypochlorous acid formulation is applied for a prolonged period of time, particularly but not exclusively in the case of treatment of a chronic condition. Generally, a chronic condition is a condition that will not be eliminated even with therapy, and thus the therapy is intended to reduce, inhibit, or prevent (by means of prophylactic treatment), inflammatory symptoms, thereby managing the condition. Prolonged use generally includes treatment for at least about six months, at least about one year, at least about two years, or more. The hypochlorous acid formulation may be used continuously in some embodiments.

In certain embodiments of the present invention, the hypochlorous acid is formulated or administered in combination with another therapeutic agent, including one or more of a corticosteroid, vitamin D ointment (or vitamin D analogue), retinoid, analgesic, immunosuppressant, topical chemotherapy, and anti-infectives (e.g., antibiotic or anti-fungal). Non-limiting examples of therapeutic agents include anti-microbial agents such as antibiotics, antivirals, anti-fungal and anti-parasitics, immune-modulators/suppressants anti-inflammatory agents, anti-histamines, analgesics, local anesthetics, anti-oxidants such as vitamins, and moisturizing agents. For example, the hypochlorous acid may be formulated or administered with antibiotics such as bacitracin, neomycin, neosporin, framycetin, fusidic acid, chloramphenicol, gentamicin, tobramycin, ceftriaxone, sulfacetamide, erythromycin, gentamicin, ciprofloxacin, ofloxacin, cefoxitin, cefotaxime, spectinomycin, tetracycline, doxycycline, and azithromycin; anti-virals such as acyclovir, valacyclovir, famciclovir, and oseltamivir; anti-fungals such a as ketoconazole, fluconazole, itraconazole, voriconazole, terbinafine, and nystatin; anti-parasitics such as metronidazole, ivermectin, pyrantel pamoate, albendazole, and atovaquone-proguanil; immune-modulators/suppressants such as thalidomide, lenalidomide, apremilast, cyclosporine, prednisone, prednisolone, and tacrolimus; corticosteroids, and NSAIDs such as aspirin, ibuprofen, naproxen sodium, celecoxib; anti-histamines such as diphenhydramine, loratadine, fexofenadine, cimetidine, ranitidine, olopatadine, ciproxifan, and cromoglycate; analgesics such as acetaminophen/paracetamol, buprenorphine, codeine, meperidine, and tramadol; local anesthetics such as epinephrine, lidocaine, bupivacaine, and benzocaine; anti-oxidants such as vitamin A & E; topical vitamin D ointment, moisturizing agents such as silicones, emollients, lanolin, mineral oil, urea, alpha-hydroxy acids, glycerine, fatty acids, ceramides, collagen or keratin.

The hypochlorous acid formulation contains hypochlorous acid and other oxidizing species in amounts as already described (e.g., available free chlorine or AFC), and is maintained at a skin-friendly pH that provides predominately HOCl as the reactive oxygen species (e.g., from about 5 to about 7). The formulation further comprises components to render the formulation shelf-stable and to provide the desired physical characteristics for topical treatment of skin.

The composition may comprise a pharmaceutically acceptable carrier. Non-limiting examples of suitable carriers include hectorite, silicates, fluorosilicates, bentonite, oil emulsions, cyclomethicone, polyvinyl alcohol, povidone, hydroxypropyl methyl cellulose, poloxamers, carboxymethyl cellulose, hydroxyethyl cellulose, and purified water. The composition may also include various other ingredients, such as tonicity agents, buffers, surfactants, co-solvents, viscosity building agents, preservatives, and other therapeutic agents.

Examples of viscosity enhancing agents include, but are not limited to: pharmaceutically-acceptable silicates for topical application, polysaccharides, such as hyaluronic acid and its salts, chondroitin sulfate and its salts, dextrans, various polymers of the cellulose family; vinyl polymers; and acrylic acid polymers, etc. For example, the composition may exhibit a viscosity of 1 to 400,000 centipoises ("cps"). In some embodiments, the composition is a hydrogel comprising a silicate-based carrier (e.g., fluorosilicate carrier). For example, the silicate can comprise a fluorosilicate salt such as sodium magnesium fluorosilicate or sodium lithium magnesium fluorosilicate. The hypochlorous acid solution can be used as a dispersing media with the silicate carrier to prepare the hydrogel. The formulation may be a hydrogel having a conductivity of from about 0.5 mS/cm to about 12 mS/cm, such as from about 1 mS/cm to about 10 mS/cm in some embodiments. The hydrogels may be prepared from silicate-based carriers, such as 0.5% to about 5% sodium magnesium fluorosilicate, and may employ an additional buffer for targeting the pH. An exemplary buffer is phosphoric acid or a combination of monosodium phosphate and phosphoric acid.

Regarding tonicity agents, such agents may be employed to adjust the tonicity of a composition. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added and the type of composition. The hypochlorous acid formulation may be hypertonic, hypotonic, or isotonic with respect to physiological fluids, but in some embodiments is hypotonic. The formulation may contain varying levels of salinity, such as from 0.01 to about 2.0%. In some embodiments, the formulation contains from about 0.02% to about 0.9% w/v NaCl. In some embodiments, the formulation contains from about 0.01 to 2.0% w/v one or more salts, such as a halide salt, e.g. NaCl, KCl, or a mixture of salts or halide salts. The salt, or halide salt may be a salt of an alkali metal or alkaline earth metal, such as sodium, potassium, calcium, or magnesium.

Regarding buffers and pH adjusting agents, sodium phosphates, potassium phosphates, potassium carbonate, sodium bicarbonate, sodium borate or boric acid, phosphoric acid, or other suitable acid may be added to the compositions to achieve a target pH and/or prevent pH drift under storage conditions. The particular concentration will vary, depending on the agent employed. Preferably, however, the buffer or pH adjusting agents will be chosen to maintain a target pH within the range of pH 4-7 or a range as described herein. In some embodiments, the formulation is a hydrogel employing a silicate-based carrier, comprises sodium bicarbonate (e.g., from 500 to 2000 mg/L) to stabilize the HOCl as described more fully below, and comprises phosphoric acid to target a slightly acidic pH (e.g., from 5 to 6.5). The formulation may have a viscosity of from about 500 to about 50,000 cP, such as from about 1000 to about 40,000 cP, or from 1000 to about 30,000 cP. The formulation in some embodiments has a conductivity of less than 10 mS/cm, such as from about 0.5 to about 5 mS/cm, such as from 0.5 to about 3 mS/cm, or about 1 or about 2 mS/cm in some embodiments.

Regarding a surfactant, various surfactants useful in conventional formulations may be employed. Exemplary surfactants include CREMOPHOR EL, lauramine oxide, myristyl dimethylamine oxide, polyoxyl 20 ceto stearyl ether, polyoxyl 40 hydrogenated castor oil, polyoxyl 23 lauryl ether and poloxamer 407.

Regarding preservatives, no additional antimicrobial agent is required, since the HOCl will function as a preservative.

Hypochlorous acid is highly unstable, a problem made more difficult when using higher strength solutions (e.g., above a few hundred ppm AFC) as well as other formulation ingredients which are often destabilizing. Thus, in some embodiments, the formulation includes a stabilizing amount of dissolved inorganic carbon (DIC) as disclosed in U.S. Pat. No. 8,871,278, which is hereby incorporated by reference in its entirety. For example, the formulation employs a stabilizing amount of DIC, which may be incorporated as a bicarbonate or carbonate of alkali or alkaline earth metal, such as, for example, sodium, potassium, calcium, or magnesium. In some embodiments, the bicarbonates or carbonates are added prior to the formation of hypochlorous acid (e.g., by electrochemical treatment), and in other embodiments, the bicarbonates or carbonates are added after electrochemical treatment. For example, the bicarbonate(s) or carbonate(s) may be contained in the precursor aqueous solution (e.g., water) or dry electrolyte, and/or incorporated in the electrolyzed solution or during formulation.

The DIC is incorporated at a "stabilizing amount," which can be determined with reference to the change in the pH or AFC content of the formulation over time. Generally, the formulation is considered stabilized if the amount of AFC does not drop below about 75% of the initial value over a period of about 6 months. In certain embodiments, the AFC content is stabilized for at least one year from the production date of the formulation. Further, the stability of the formulation may be determined with reference to the pH. Generally, the formulation is considered stabilized if the pH does not vary by 1 unit over a period of about 6 months. In certain embodiments, the pH is stabilized for at least one year from the production date of the formulation. The formulation should be stored at 25° C. or at 20° C. or less for greater stability. 25° C. and 20° C. are the reference temperatures for determination of stability. For stability testing, solutions or formulations are packaged in HDPE bottles, stored in the dark, and kept unopened. The formulation may be stored at 4° C. until use in some embodiments.

The stabilizing amount of DIC (e.g., carbonate or bicarbonate) can be determined with reference to the AFC content. For example, in certain embodiments, the stabilizing amount of the carbonate or bicarbonate is at a molar ratio of from about 5:1 to 1:5 with respect to the AFC level, or from about 2:1 to about 1:2 with respect to the AFC level. In some embodiments, the bicarbonates or carbonates are present in at least equimolar amounts with respect to the AFC content (e.g., hypochlorous acid content). In still other embodiments, the DIC (e.g., bicarbonate or carbonate) is present at about 5:1, about 4:1, about 3:1, about 2:1, about 1:1, about 1:2, about 1:3, about 1:4, or about 1:5 with respect to AFC content. In various embodiments, other buffering components such as phosphate buffers are also employed. For example, for formulation having an AFC content of from about 200 ppm to about 500 ppm, carbonate or bicarbonate may be present at an amount of from about 300 mg/L to about 1500 mg/L to stabilize the formulation. In certain embodiments, such formulations are stabilized by incorporating from about 400 to about 1000 mg/L of carbonate or bicarbonate. In certain embodiments, the formulation has AFC in the range of 500 to 1000 ppm, comprises sodium bicarbonate in the range of about 500 to about 2000 mg/L, has a pH in the range of 5 to 7, and comprises sodium magnesium fluorosilicate from 2 to 5% (e.g., about 3% or about 4%).

Without being bound by theory, dissolved inorganic carbon (DIC), which generally includes carbonates, bicarbonates, carbonic acid and dissolved $CO_2$, provides low or minimal buffering capacity in the pH range targeted by the solutions and formulations described herein. Nevertheless, these solutions are effectively stabilized, such that the solutions and compositions are not dependent on "on-demand" production. The stabilizing effect can be due to, in-part, free radical scavenging ability of DIC to thereby slow the decomposition of HOCl.

While the hypochlorous acid may be produced chemically in accordance with some embodiments (e.g., by acidification of hypochlorite), the hypochlorous acid may also be produced electrochemically. The electrochemical production of hypochlorous acid is by treatment of halide-based electrolytes in a diaphragm-type electrolytic cell. Electrochemical treatment of saline is described, for example, in U.S. Pat. Nos. 7,303,660, 7,828,942, and 7,897,023, which are hereby incorporated by reference in their entireties.

The stabilized formulation may be packaged for sale, using any suitable container, such as any suitable plastic or glass bottles, or bags (e.g., plastic bags), tubes, or cans (e.g., spray or aerosol). Certain container materials may provide advantages in shelf-life. In certain embodiments, the packaging material has minimal gas permeability (e.g., are non-permeable), including by species such as $CO_2$ and $O_2$. Thus, these containers maintain the stabilizing amount of dissolved inorganic carbon, without losing the stabilizer in the form of $CO_2$. The containers may be transparent, or opaque so that they are impenetrable by light. While the volume of the container has been considered to impact stability and shelf-life, the formulations described herein may be in the range of about 50 ml to about 2 liters, or from about 100 ml to about 1 liter. Exemplary containers have a unit volume of about 50 ml, about 100 ml, about 125 ml, about 250 ml, about 0.5 liter, about 1 liter, about 2 liters, about 3 liters, about 4 liters, about 5 liters, or about 10 liters.

EXAMPLES

Example 1: Hydrogel Formulations

A hydrogel formulation containing a stabilized hypochlorous acid solution was developed. Bicarbonate or dissolved inorganic carbon has only a minimal effect on the ionic strength or electroconductivity of the solution. Thus, in addition to stabilizing a HOCl solution in the pH range of about 4 to about 7.5 (e.g. about 6), bicarbonate or carbonate do not affect the ionic strength at the targeted pH, making it possible to use hypochlorous acid with more than 200 ppm of available free chlorine as the dispersing media in a gel formulation, especially where low ionic strength is important.

A low ionic strength hypochlorous acid solution (conductivity ≤1 mS/cm (i.e., millisiemens per centimeter)), AFC=300 ppm, pH 5.3 was used for a hydrogel formulation containing 3% sodium magnesium fluorosilicate. More than 4% sodium magnesium fluorosilicate was required for the production of a hydrogel of equal viscosity made out of 8 mS/cm of HOCl with equal pH and AFC content. A lower ionic strength HOCl solution as a dispersing media allows for the addition of other buffering agents for pH optimization in the final product without negative effects on physical appearance and product stability. Due to the fact that the gelling agent is a dry buffer itself, the ability to add other buffers for pH optimization in a final product can be beneficial.

In another example, hypochlorous acid solution, AFC 350 ppm, pH 5.3, salinity 4 g/l (conductivity 8 mS/cm) was used for the production of a hydrogel containing 4% $F_{12}MgNa_2Si_2$ (sodium magnesium fluorosilicate). The hydrogel produced had a viscosity of 33,000 centipoises (cP) and a pH of 8.2. To bring the pH to a "skin-friendly" range phosphoric acid was added as a buffering agent. The final hydrogel had a shift in pH over time from pH 6 to 6.8. Additional buffer is limited by gel viscosity as it shifts to 220 cP with a conductivity increase to 10 mS/cm.

Low ionic strength hypochlorous acid, AFC=370 ppm, was produced by electrochemical treatment of sodium chloride substantially as described in U.S. Pat. No. 7,897,023 (which is hereby incorporated by reference in its entirety), and collected in a container with dry sodium bicarbonate, equivalent to 500 ppm of $NaHCO_3$ as an initial form of dissolved inorganic carbon (DIC). An HOCl pH 5.2 and conductivity 0.8 mS/cm produced by this process was used as dispersing media for a gel preparation. 3% of sodium magnesium fluorosilicate was used as a gelling agent. Hydrogel formed with a viscosity of about 10,000 cP in less than 25 minutes with an initial pH of 8.4 and a conductivity of about 1 mS/cm. Phosphoric acid was added in the amount of less than 0.25% to bring the pH of the hydrogel down to a skin-friendly range (about pH 5.5-5.8). A hydrogel with a viscosity above 2,000 cP was formed.

In another example, low ionic strength hypochlorous acid (AFC=1,500 ppm) was produced as described in U.S. Pat. No. 7,897,023, and with injection of sodium bicarbonate solution (70 g/L) into the HOCl solution stream. An HOCl solution pH 5.2 and conductivity 2.0 mS/cm produced by this process was used as a dispersing media for a gel preparation. 4% of sodium magnesium fluorosilicate was used as a gelling agent. 2% Cyclomethicone was added as an emollient after all gelling agent was dispersed. Hydrogel formed with a viscosity of about 100,000 cP in less than 25 minutes with an initial pH of 8.4. Phosphoric acid, 2%, was slowly added in the amount of less than 0.5% to bring the pH of the hydrogel down to a skin-friendly range (about pH 5.5-5.8). A hydrogel with a viscosity above 20,000 cP was formed.

Low ionic strength hypochlorous acid (AFC=1,500 ppm) was produced as described in U.S. Pat. No. 7,897,023, including with injection of sodium bicarbonate solution (70 g/L) into HOCl solution stream. An HOCl solution pH 5.0 and conductivity 2.0 mS/cm produced by this process was used as a dispersing media for a preparation of gel with a combination of sodium magnesium fluorosilicate and magnesium aluminum silicate, 3:1, as gelling agent composition.

Example 2: Evaluation of Itch Reduction

In an investigator—blinded, randomized study, hypochlorous acid composition in the form of gel was evaluated for reduction of inflammation, by means of itching reduction. 30 subjects aged 12 to 75 years old with mild to moderate atopic dermatitis participated over a period of 3 days. The patients, 20 subjects, treated with hypochlorous acid composition, ≤450 ppm AFC, were compared to 10 untreated control subjects. The evaluation included an assessment of tolerability by investigator and participant.

Overall irritation, stinging, burning and itching on a 5-point ordinal scale were evaluated on day 1 (baseline visit), day 2 and day 3. Investigator assessment was calculated as the mean of 5-point scale for erythema, desquamation, lichenification, overall irritation, and excoriation. Subject queries were based on stinging, burning and itching at day 1, day 2, and day 3. Incidence of all adverse events, including serious adverse events, local skin reaction, and adverse events leading to discontinuation, were documented.

Treatment with the HOCl composition effectively reduced itch in subjects with mild to moderate atopic dermatitis as early as day 1.

The HOCl treatment group had significantly reduced itch compared with the Untreated group at Day 3 ($p=0.007$).

Treatment with the HOCl composition at least BID was very well tolerated, and there were no serious adverse events and no treatment-related discontinuations.

Example 3: Case Study Evaluation of Inflammation Reduction

An evaluation of inflammation reduction by means of itching reduction and skin quality improvement was conducted on a 4 year old male treated with HOCl gel. The patient had eczema of the palmar aspect of the patient's hands and plantar aspect of the feet. The patient experienced severe itching, severe erythema (beet redness) to eschar formation, cracking, yellow plaques/hardening of skin and peeling of the skin over the course of two months. As a first line of therapy, the patient was prescribed Hydrocortisone Valerate Ointment USP, 0.2%, a topical corticosteroid twice daily to the affected areas. After 4 weeks of treatment twice daily with corticosteroids, the patient had no resolution of symptoms.

The patient was taken off the topical corticosteroid and instead treated with hypochlorous acid composition ≤450 ppm AFC, twice daily to the affected areas.

Treatment with HOCl composition effectively reduced symptoms in a subject with moderate eczema as early as Day 1.

At both Day 1 and Day 3, the patient exhibited marked reduction of symptoms including: reduction of itch, reduction of erythema (reduction of redness), skin wound healing (reduction of cracks), softening of plaques and movement towards normal skin color, and reduction of peeling.

Treatment with HOCl composition at least BID was very well tolerated.

The patient went on to complete resolution of all symptoms over the course of two weeks BID treatment.

There were no serious adverse events and no treatment related discontinuations.

The patient and guardian reported increased "ease-of-use" with the HOCl composition in form of gel vs treatment with corticosteroids, as there were no warnings regarding getting the product in/or near the eyes, nose or mouth, which is difficult when the product must be applied to the hands and fingers.

Example 4: Reduction in Hyperemia in an Animal Model

HOCl solution was studied for topical treatment of redness and itching associated with allergic conjunctivitis in systemic sensitization model. In this model, a systemic sensitization with an allergen (Short Ragweed, SRW) was followed by topical challenge with the same allergen. The objective of this study was to evaluate the effectiveness of three hypochlorous acid formulations in reducing the signs and symptoms associated with ocular allergic conjunctivitis.

The results of this study indicate the hypochlorous acid was able to reduce hyperemia in this model of allergic conjunctivitis in a dose dependent manner. The 500 ppm and 1000 ppm hypochlorous acid significantly reduced redness in the eyes of balb/c mice similar to that of a steroid (prednisolone, 1%). The controls in this study worked as they should, with the vehicle control producing a high amount of hyperemia post challenge and the prednisolone group maintaining low redness scores throughout all challenges. As expected, the mast cell stabilizer group (olopatadine) was able to significantly reduce hyperemia after the first challenge, but loses efficacy over time. The high concentration hypochlorous acid groups were able to significantly reduce hyperemia throughout the entire challenge process, whereas the lowest concentration of 100 ppm could not reduce redness.

All references cited herein are incorporated by reference in their entireties.

The invention claimed is:

1. A method for treating pruritus involving neurogenic or psychogenic itch, comprising:
    applying to affected areas of the skin of a subject in need thereof a hypochlorous acid formulation having an amount of hypochlorous acid effective to reduce or inhibit the neurogenic itch or psychogenic itch, wherein the hypochlorous acid formulation comprises at least 300 ppm of available free chlorine (AFC), and wherein AFC is at least 80% hypochlorous acid relative to the total of hypochlorous acid, hypochlorite, and $Cl_2$ in the hypochlorous acid formulation, wherein the affected areas are intact skin.

2. The method of claim 1, wherein the subject has prurigo nodularis.

3. The method of claim 1, wherein the neurogenic itch is a neurogenic itch secondary to a hematological disorder, lymphoproliferative disease, cholestasis, hepatic disease, endocrine disease, or chronic kidney disease.

4. The method of claim 1, wherein the hypochlorous acid formulation has at least 500 ppm of AFC.

5. The method of claim 1, wherein the hypochlorous acid formulation has at least 700 ppm of AFC.

6. The method of claim 1, wherein the hypochlorous acid formulation has at least 1000 ppm of AFC.

7. The method of claim 1, wherein the hypochlorous acid formulation has AFC in the range of 500 ppm to 1500 ppm.

8. The method of claim 1, wherein the hypochlorous acid formulation has pH of from 5 to 7.

9. The method of claim 1, wherein the hypochlorous acid formulation has pH of from 5.4 to 6.4.

10. The method of claim 1, wherein the hypochlorous acid formulation has pH of from 5.0 to 6.4.

11. The method of claim 1, wherein the hypochlorous acid formulation is applied to the affected areas of the skin from 1 to 10 times daily.

12. The method of claim 1, wherein the hypochlorous acid formulation is applied to the affected areas of the skin from 1 to 3 times daily.

13. The method of claim 1, wherein the hypochlorous acid formulation is applied periodically to control symptoms or flare-ups.

14. The method of claim 1, wherein the hypochlorous acid formulation is a hydrogel formulation.

15. The method of claim 14, wherein the hypochlorous acid formulation further comprises:
    a pharmaceutically-acceptable silicate carrier for topical application; and
    sodium bicarbonate at from 500 mg/L to 2000 mg/L.

16. The method of claim 15, wherein the silicate carrier is sodium magnesium fluorosilicate or sodium lithium magnesium fluorosilicate.

17. The method of claim 14, wherein the hypochlorous acid formulation has a conductivity of from about 0.5 mS/cm to about 12 mS/cm.

18. The method of claim 14, wherein the hypochlorous acid formulation has a conductivity of from about 1 mS/cm to about 10 mS/cm.

* * * * *